United States Patent [19]

Malenchek

[11] Patent Number: 5,273,541
[45] Date of Patent: Dec. 28, 1993

[54] SAFETY SYRINGE

[76] Inventor: Robert Malenchek, 279 Sunnymead Rd., Somerville, N.J. 08876

[21] Appl. No.: 923,595

[22] Filed: Aug. 3, 1992

[51] Int. Cl.$^5$ .............................................. A61M 5/00
[52] U.S. Cl. ..................................... 604/110; 604/195
[58] Field of Search ............... 604/110, 195, 198, 263, 604/187, 218

[56] References Cited

U.S. PATENT DOCUMENTS

| | | | |
|---|---|---|---|
| 4,850,968 | 7/1989 | Romano | 604/110 |
| 4,927,416 | 5/1990 | Tomkiel | 604/198 |
| 4,932,947 | 6/1990 | Cardwell | 604/198 |
| 5,026,354 | 6/1991 | Kocses | 604/195 |
| 5,066,277 | 11/1991 | Carrell et al. | 604/110 |

Primary Examiner—John D. Yasko
Attorney, Agent, or Firm—Omri M. Behr; Matthew J. McDonald

[57] ABSTRACT

A safety syringe has a hollow shield with a plunger opening on one end and a needle opening on the other end. At least one locking lug is mounted at the plunger opening. The syringe also has a lumen that is telescopically mounted at least partially within the shield. The lumen has a catch for engaging the locking lug. A needle attached to the lumen is aligned with the needle opening of the shield. An urging means is mounted in the shield to urge the lumen and to retract the needle into the shield. A plunger has an inner end slidably mounted in the lumen and an outer end mounted through the plunger opening. The outer end of the plunger has an extension for engaging and deflecting the locking lug to release the catch, which allows the urging means to retract the needle into the shield.

13 Claims, 4 Drawing Sheets

SAFETY SYRINGE

BACKGROUND OF THE INVENTION

The present invention relates to a syringe, and in particular, to a mechanism for locking a needle inside a hollow shield to prevent repeated use.

Contaminated needles have become increasingly dangerous to people in the medical profession due to the increase in people infected with the AIDS virus and other infectious diseases. Therefore, various syringes have been developed to cover the needles after use. Often, the needle retracts to reduce the risk of pricks by an exposed contaminated needle.

In addition, the re-use of a syringe by people addicted to injectable drugs contributes to the spread of disease. Therefore, it is also desirable to have a needle that can only be used once to prevent drug users from sharing contaminated needles. Many improved syringes have been developed that provide for the covering of a needle after use. However, existing designs often have relatively complicated constructions. In addition, some of these so called "single-use" syringes can be returned to working order with minimal effort.

U.S. Pat. No. 4,973,316 shows a one-handed retractable safety syringe where the needle retracts into the medicine barrel by further depressing a plunger after the medicine has been injected. This overtravel disengages two triggers, thereby releasing a spring that pushes the needle holder and needle back into the barrel. U.S. Pat. No. 4,978,343 shows a similar structure but including a pimple on the needle holder that rocks the needle after retraction into the housing to prevent re-extension. In both patents the release mechanism is located inside the medicine barrel near the needle end. Such a configuration is relatively frail since it must be small enough to fit inside the medicine barrel. Moreover clearing a jam in the inaccessible trigger mechanism is difficult with an internal mechanism. In addition, having moving parts inside the barrel where the medicament is held could cause contamination if chips or fragments break off.

U.S. Pat. No. 5,049,133 shows a single-use safety syringe with a needle mounted in a head that is held by teeth-like triggers. When a plunger reaches an extreme position the triggers release the needle and head which then retract into the hollow cavity in the plunger under the urging of a compression spring. Again, the trigger mechanism is internally located inside the medicine barrel at the needle end. Accordingly, the mechanism would be prone to jamming and fragment contamination.

In international patent PCT/EP89/01408, the needle of a single-use syringe is held in a working position by a retaining member. After use, the retaining member is released by further pressing the plunger which allows a spring to retract the needle into the body. This rather complicated device requires the cooperation of a large number of internally located moving parts having the disadvantages noted above.

Other patents, not analyzed in detail herein, have a releasable needle shield, and may require two hands to lock the needle in the working position before use and to release the needle after use. The needle may be locked into place either by rotating the shield or operating a button or clip. See U.S. Pat. Nos.: 4,900,311, 5,013,301, 4,850,977, 4,927,416, 4,929,237, 4,955,868 and 5,049,136.

Accordingly there is a need for an effective safety syringe employing a retractable needle that is reliable, simple to clear if jammed, and unlikely to suffer from fragment contamination.

SUMMARY OF THE INVENTION

The present invention relates to a safety syringe, and in particular to a mechanism for automatically retracting the needle after use into a safety shield so the needle is no longer exposed.

It is an object of this invention to decrease the risk of harm to the user from a hypodermic syringe by providing a syringe whose needle is automatically retracted into a housing after a dose has been injected, thereby preventing the user from being pricked by the needle.

It is a further object of this invention to retract the needle back into a shield in such a way that re-use is made difficult.

It is yet a further object of this invention to provide a safety syringe that is reliable, efficient, and easy to manufacture.

An additional object of the invention is to have a syringe with a catch mechanism allowing for easy clearing of a jam.

In accordance with the illustrated embodiments demonstrating features and advantages of the present invention, there is provided a syringe having an outer hollow shield. The shield has a plunger opening and a needle opening. At least one locking lug is mounted at the plunger opening. A lumen telescopically mounted at least partially within the shield, has a catch for engaging the locking lug. A needle is attached to the lumen and is aligned with the needle opening in the shield. In addition, a plunger has an inner end slidably mounted into the lumen and an outer end mounted through the plunger opening. Mounted in the shield is an urging means mounted for urging the lumen and retracting the needle into the shield. The outer end of said plunger has an extension for engaging and deflecting the locking lug to release the catch. Thus the urging means can retract the needle into the shield.

By employing a device of the foregoing type, an improved safety syringe is achieved. In a preferred embodiment, a shield is released from a lumen by over-depressing a plunger into the lumen. The aforementioned extension on the plunger, preferably a disc-shaped tab with beveled ends, deflects a locking lug and releases the shield. The aforementioned urging means can include a compression spring mounted between the shield and the lock. Thus, the extension on the plunger can deflect the locking lug, so the spring will retract the lumen and its lock into the shield, sending the lock through the plunger opening. The lock can then engage the locking lugs thereby securing the needle in the shield.

BRIEF DESCRIPTION OF THE DRAWINGS

The above description, as well as other objects, features and advantages of the present invention will be more fully appreciated reference to the following detailed description of the presently preferred but nonetheless illustrative embodiments in accordance with the present invention when taken in conjunction with the accompanying drawings, wherein.

DETAILED DESCRIPTION OF THE PREFERRED EMBODIMENTS

Figure 1:
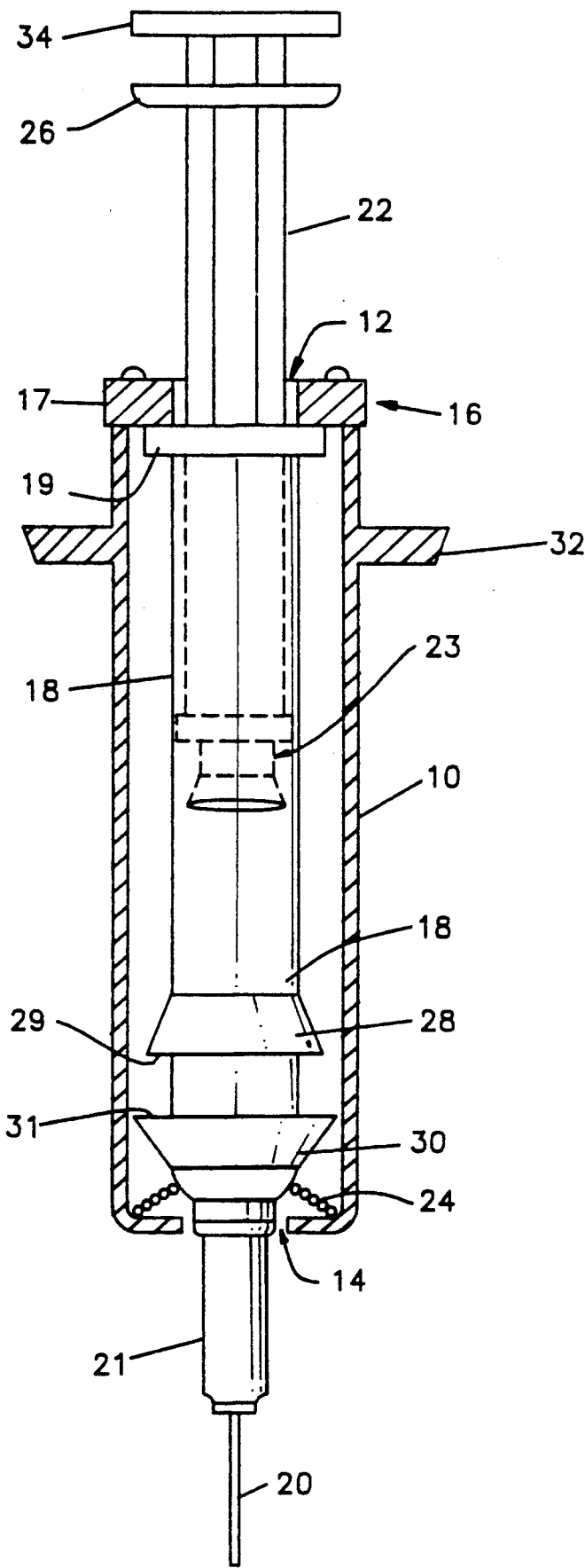
FIG. 1 is a side view, partially in section, of a syringe according to the principles of the present invention.

Referring to FIGS. 1–4, a single-use safety syringe has an elongated hollow shield 10. Shield 10 has a tube-like configuration with a plunger opening 12 on one end and a needle opening 14 on the opposite end. Shield 10 is shaped as a hollow cylinder but may be a hollow prism or other shape in different embodiments. Shield 10 can be transparent plastic, glass and the like. Finger supports 32 extend transversely from shield 10 near plunger opening 12. Finger supports 32 are preferably rounded (see FIG. 3) with beveled edges, although rectangular and other shapes are possible.

Shield 10 has six locking lugs 16 located at the plunger opening. Lugs 16 are grouped into two trios. Each trio is equiangularly spaced by 45 degrees. The trios are positioned on opposite sides of the plunger opening 12. This arrangement allows for easy deflection, although the number, shape and pattern of the locking lugs can be varied.

Figure 5:
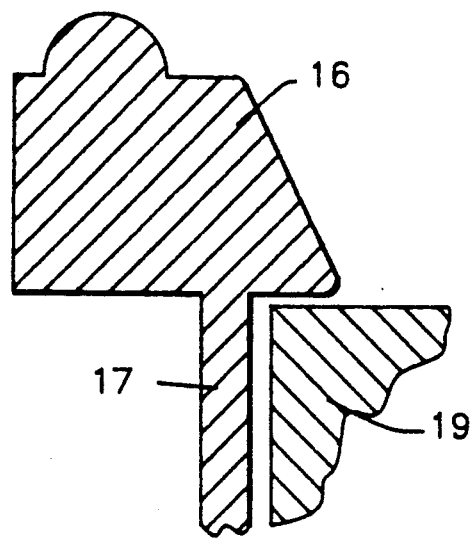
FIG. 5 is a detailed, cross-sectional view of the locking lug of FIG. 1 holding a catch.

Locking lugs 16 are preferably rectangular solids with a concave, cylindrically shaped inside end. As shown in FIG. 5 the inside face of lug 16 is slanted. The lugs, however, can have various other solid shapes including cylindrical, spherical, prismatic, etc. Lugs 16 are mounted atop relatively flexible slender supports 17.

Lumen 18 is shown as a hollow cylinder telescopically mounted at least partially within shield 10. Lumen 18 has a catch 19 for engaging locking lugs 16 in the shape of a cylindrical, annular flange. Lumen 18 is preferably made of plastic, but can be made out of other materials such as glass. Lumen 18 preferably has gradations marked on its outside to facilitate determining the volume of medicine being dispensed. Alternatively, gradations can be marked on shield 10.

Needle 20 is secured to holder 21. Needle 20 is attached to lumen 18 through holder 21 and is aligned with the needle opening 14 in shield 10. Needle opening 14 is sized to encircle holder 21 when the syringe is in the working condition.

Lock 28 (also referred to as a locking means) is a frustro-conical skirt encircling lumen 18. Stop 30 is a frustro-conical flange encircling lumen 18. Stop 30 is located between and spaced from needle 20 and lock 28. The base 29 of lock 28 faces the base 31 of stop 30. A compression spring 24 (referred to as an urging means) is mounted in shield 10 between stop 30 and the needle end of the shield. Stop 30 is preferably frustro-conical and has a base diameter slightly smaller than the diameter of the shield. Stop 30 can have a variety of different shapes such as tetrahedral or cylindrical. Lock 28 is also frustro-conical, is smaller than stop 30 and can also have a variety of shapes.

Plunger 22 has an inner end 23 slidably mounted in lumen 18. Plunger 22 is also mounted within plunger opening 12. The inner end 23 of plunger 22 has a cruciform midsection and a gasket to pressurize and dispense medicine in lumen 18. The outer end of the plunger 22 has a thumb flat 34 and an extension 26. Extension 26 is sized to engage and deflect locking lugs 16 when thumb flat 34 is over-depressed.

To facilitate an understanding of the principles associated with the foregoing apparatus, its operation will now be briefly described. The syringe is delivered in the condition shown in FIG. 1, with needle 20 exposed. As shown in FIG. 5 catch 19 is held by lug 16 at this time.

First the syringe is loaded from an ampoule (not shown) in the usual fashion. Essentially, needle 20 is inserted into an ampoule with the ampoule and syringe inverted. The medicament is withdrawn by pulling plunger 22 partially out of lumen 18 until the appropriate amount of medicine has been obtained. The needle is then pulled from the ampoule. Next, the user slightly depresses thumb flat 34 to remove any excess air. The syringe is now filled and ready for use.

In the preferred embodiment, when injecting, the user's fingers go around each of the finger supports 32 while the thumb is positioned on thumb flat 34. The needle 20 is then inserted into a patient and plunger end 23 is driven toward needle 20, thereby injecting the medicament. The needle can then be removed from the patient.

Figure 2:
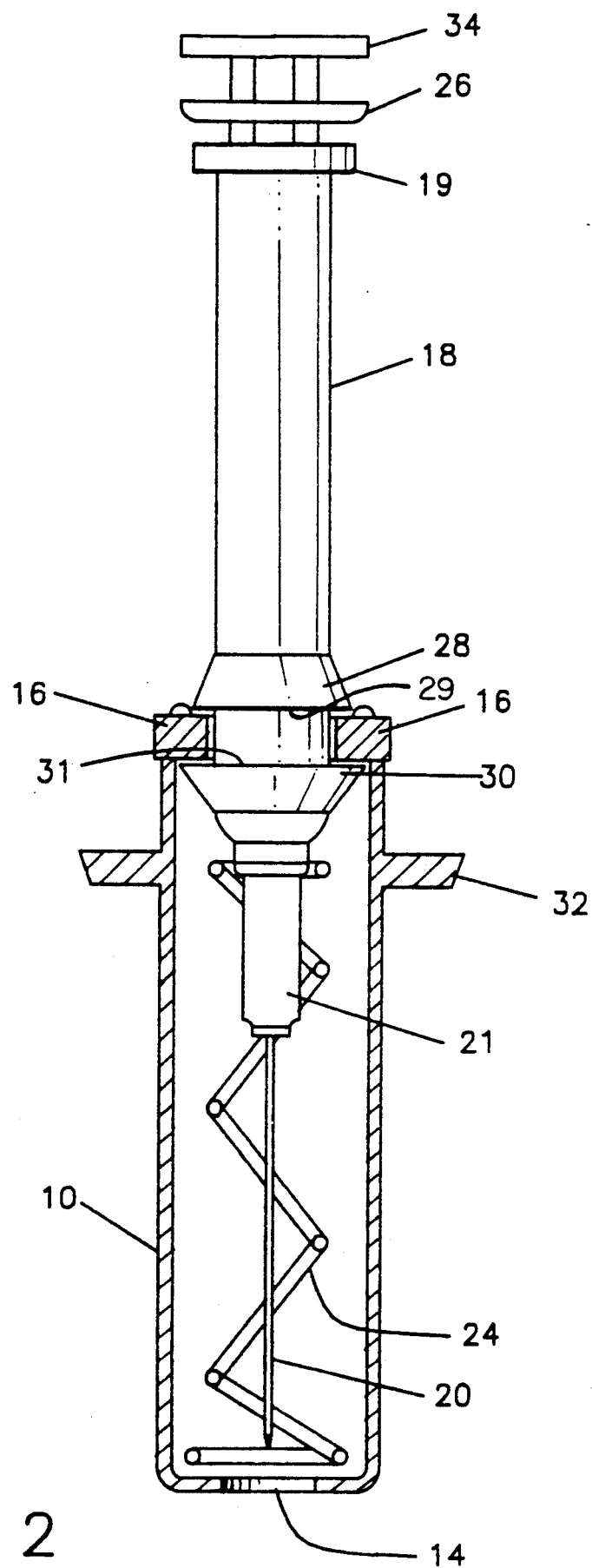
FIG. 2 is a side view of the syringe of FIG. 1 after the needle retracts into the shield.
Figure 3:
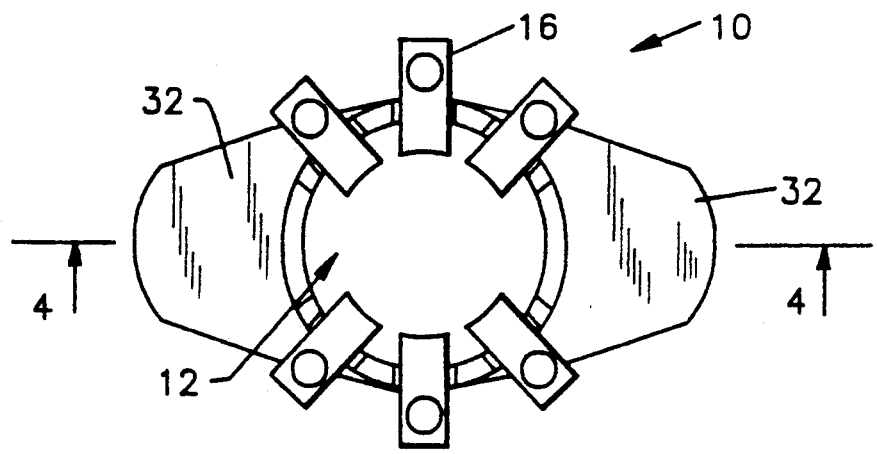
FIG. 3 is an end view of the shield of FIG. 1.
Figure 4:
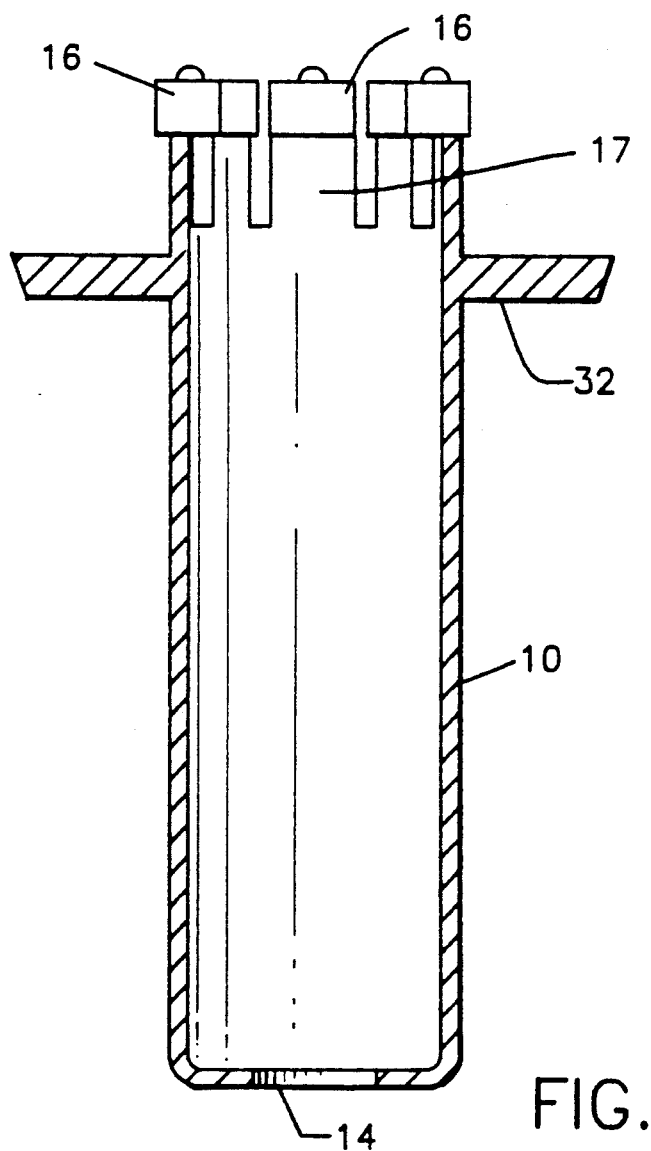
FIG. 4 is a cross-sectional view taken along line 4—4 of FIG. 3.
Figure 6:
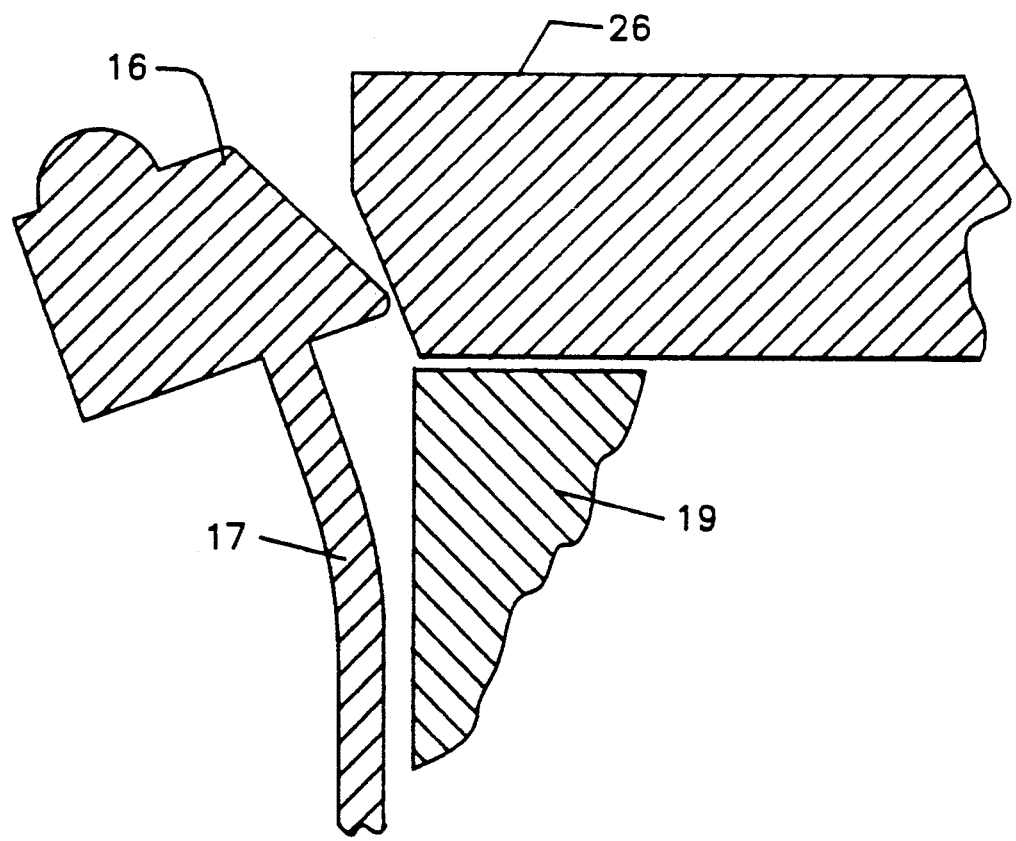
FIG. 6 is a detailed view of the beveled extension releasing the locking lug of FIG. 5.

Next, plunger 22 is depressed further to force beveled extension 26 against locking lugs 16. Further pressure causes extension 26 to spread apart locking lugs 16 of the shield 10 as shown in FIG. 6. From the detailed view of FIG. 6 beveled extension 26 deflects locking lug 16, releasing catch 19. Since the catch is located near plunger opening 12, and jamming can easily be rectified. The release of catch 19 permits the entire body of the syringe to retract into the shield by the urging of spring 24, until stop 30 engages the underside of locking lugs 16 as shown in FIG. 2. This secures needle 20 inside the shield so that the syringe can no longer be used.

As the safety syringe retracts, lock 28 enters plunger opening 12. The slanted sides of lock 28 act as a camming surface to spread lugs 16 apart. As lock 28 travels, its trailing edge eventually passes lugs 16, which then snap closed behind lock 28. This snapping locks the syringe in the safe position and makes re-use difficult. When in the safe condition of FIG. 2, the base 31 of stop 30 rests against the underside of locking lugs 16. Top lock 28 and stop 30 are separated a distance approximately equal to the thickness of the locking lugs to prevent movement. In the position shown in FIG. 2, the needle segment is locked into the shield in such a way that it can no longer be readily reactivated.

Obviously, many modifications and variations of the present invention are possible in light of the above teachings. It is therefore to be understood that within the scope of the appended claims, the invention may be practiced otherwise than as specifically described.

I claim:

1. A safety syringe comprising:
   an outer hollow shield having a plunger opening, a needle opening, and at least one locking lug mounted at said plunger opening;
   a lumen telescopically mounted at least partially within said shield and having a catch for engaging said locking lug;
   a needle attached to said lumen and aligned with said needle opening in said shield;
   urging means mounted in said shield for urging said lumen and retracting said needle into said shield;

a plunger having an inner end slidably mounted in said lumen and an outer end mounted through said plunger opening, said outer end of said plunger having an extension for engaging and deflecting said locking lug without entering said lumen to release said catch, so that said urging means can retract said needle into said shield.

2. The safety syringe of claim 1 wherein said shield includes at least one finger support projecting from said shield.

3. The safety syringe of claim 2 comprising a locking means mounted on said lumen for locking said needle in said shield upon retraction of said needle into said shield, wherein the locking means comprises:
- a lock mounted on said lumen for locking on said locking lug; and
- a stop mounted on said lumen and spaced from said lock, said stop being arranged to abut said locking lug when said catch is released.

4. The safety syringe of claim 3 wherein said lock has a wedging surface for spreading said locking lugs.

5. The safety syringe of claim 4 wherein said stop has an outside diameter slightly smaller than the inside diameter of said shield and wherein said lock is separated from said stop by approximately the thickness of said locking lugs.

6. The safety syringe of claim 5 wherein said urging means comprises a compression spring mounted between said stop and said shield.

7. The safety syringe of claim 2 wherein said extension on said plunger is disc-shaped and has a beveled edge for engaging and deflecting said locking lug.

8. The safety syringe of claim 7 wherein said locking lug comprises a plurality of rectangular members mounted at said plunger opening for engaging said catch on said lumen, said rectangular members being spreadable when engaged by said beveled edges of said extension.

9. The safety syringe of claim 8 further comprising:
- a plurality of cantilevered supports mounted at said plunger opening, said rectangular members being separately mounted on corresponding ones of said cantilevered supports.

10. The safety syringe of claim 9, wherein said finger support includes a first support and a second support oppositely projecting from said shield.

11. The safety syringe of claim 2 wherein said locking lug has a slanted face positioned to engage and be deflected by said extension.

12. A safety syringe comprising:
- an outer hollow shield having a plunger opening, a needle opening, and a plurality of locking lugs mounted at said plunger opening;
- a lumen telescopically mounted at least partially within said shield and having a catch for engaging said locking lugs;
- a needle attached to said lumen and aligned with said needle opening in said shield;
- a lock encircling said lumen;
- a stop encircling said lumen and spaced between said needle and said lock;
- a compression spring mounted between said lock and said shield; and
- a plunger having an inner end slidably mounted in said lumen and an outer end mounted through said plunger opening, said outer end of said plunger having an extension for engaging and deflecting said locking lugs to release said catch, so that said spring can retract said needle into said shield.

13. A safety syringe comprising:
- an outer hollow shield having a plunger opening, a needle opening, and at least one locking lug mounted at said plunger opening;
- a lumen telescopically mounted at least partially within said shield and having a catch for engaging said locking lug;
- a needle attached to said lumen and aligned with said needle opening in said shield;
- urging means mounted in said shield for urging said lumen and retracting said needle into said shield;
- a plunger having an inner end slidably mounted in said lumen and an outer end mounted through said plunger opening, said outer end of said plunger having an extension for engaging and deflecting said locking lug to release said catch, so that said urging means can retract said needle into said shield; and
- a locking means mounted on said lumen for locking said needle in said shield upon retraction of said needle into said shield, said locking means comprising:
- a lock mounted on said lumen for locking on said locking lug; and
- a stop mounted on said lumen and spaced from said lock, said stop being arranged to abut said locking lug when said catch is released.

* * * * *